US006358919B1

(12) United States Patent
Kanie et al.

(10) Patent No.: US 6,358,919 B1
(45) Date of Patent: Mar. 19, 2002

(54) POLYMER COMPOUNDS COMPRISING GLYCOSPHINGOSINE

(75) Inventors: Osamu Kanie; Chi-Huey Wong, both of Saitama; Hiroshi Kamitakahara, Kyoto, all of (JP)

(73) Assignee: The Institute of Physical and Chemical Research, Saitama (JP)

( * ) Notice: Subject to any disclaimer, the term of this patent is extended or adjusted under 35 U.S.C. 154(b) by 0 days.

(21) Appl. No.: 09/109,870

(22) Filed: Jul. 6, 1998

(30) Foreign Application Priority Data

Sep. 12, 1997 (JP) .............................................. 9-247937
Jan. 5, 1998 (JP) ........................................... 10-000194

(51) Int. Cl.$^7$ .......................... A61K 38/16; C07K 1/00; C08B 37/00
(52) U.S. Cl. .......................... 514/8; 530/345; 530/395; 530/402; 536/55.1; 536/55.2; 536/69
(58) Field of Search .............................. 514/8; 530/345, 530/395, 402; 536/401, 55.1, 55.2, 69

(56) References Cited

U.S. PATENT DOCUMENTS

| 5,571,900 A | * | 11/1996 | Wiegand et al. | 536/4.1 |
| 5,639,786 A | | 6/1997 | Itzstein et al. | 514/459 |
| 5,648,379 A | | 7/1997 | Itzstein et al. | 514/459 |

FOREIGN PATENT DOCUMENTS

| JP | 11147951 | 6/1999 |
| JP | 11343295 | 12/1999 |

OTHER PUBLICATIONS

English Language Translation of the Jul. 10, 1997 Abstract from the Japanese Carbohydrote Symposium, *Angew, Chem. Int. Ed.*, 37, No. 11, pp. 1524–1528, 1998.*

Enlish Language Abstract of JP 11–14795A.

Enlish Language Abstract of JP 11–343295A.

Suzuki et al., "Structural Determination of Gangliosides that Bind to Influenza A, B, and C Viruses by an Improved Binding Assay: Strain–Specific Receptor Epitopes in Sialo–Sugar Chains", Virology, vol. 189, pp 121–131 (1992).

Sun et al., "Syntheses of C–3–modified Sialyglycosides as Selective Inhibitors of Influenza Hemagglutinin and Neuraminidase", Eur. J. Org. Chem., 2000, pp 2643–2653.

Chao–Tan Guo et al., "Synthetic Sialylphosphatidylethanolamine Derivatives Bind to Human Influenza A Viruses and Inhibit Viral Infection", Glycoconjugate Journal 15, pp 1099–1108 (1998).

Mammen et al., J. Med. Chem, 38, 4179–4190, 1995.

English Language Translation of the Jul. 10, 1997 abstract from the Japanese Carbohydrate Symposium, Angew. Chem. Int. Ed., 37, No. 11, 1524–1528, 1998, including the cover sheet and a correction sheet.

Von Itzstein et al., "Rational Design of Potent Sialidase–based Inhibitors of Influenza Virus Replication", Nature, vol. 363, pp 418–423 (1993).

"FDA Talk Paper", dated Jul. 27, 1999.

* cited by examiner

*Primary Examiner*—Christopher S. F. Low
*Assistant Examiner*—Abdez A. Mohamed
(74) *Attorney, Agent, or Firm*—Greenblum & Bernstein, P.L.C.

(57) ABSTRACT

A polymer compound or a salt thereof which comprises a biodegradable polymer such as polyglutamic acid acetylated at N-terminal thereof containing a glycosphingolipid such as lysoganglioside $GM_3$, and which exerts antiviral activity against variety of viruses and is useful as an active ingredient of a medicament.

12 Claims, No Drawings

POLYMER COMPOUNDS COMPRISING GLYCOSPHINGOSINE

TECHNICAL FIELD

The present invention relates to a medicament. More specifically, the present invention relates to a polymer compound comprising a saccharide-conjugated sphingosine, and a medicament comprising the polymer compound as an active ingredient.

BACKGROUND ART

Vaccines are generally used for the prevention of viral infections. However, vaccines fail to achieve sufficient preventive effects against viruses which rapidly develop variations, such as influenza virus and AIDS virus. Accordingly, it has been desired to develop antiviral agents having satisfactory effects against the viruses developing rapid variations.

For example, it is known that the two distinct proteins that are possessed by influenza virus, i.e., sialidase and hemagglutinin, have different roles. Sialidase is an enzyme which engages in the cleavage of sialic acid residues from sialyloligosaccharides on cellular surfaces when viruses germinate from cells. Recently, a sialic acid derivative having inhibitory activity against sialidase has been developed, and a clinical application as an anti-influenza viral agent is being studied.

Hemagglutinin, a trimer protein, has a key role in the introduction of a viral genome RNA into host cells by recognizing a sialyloligosaccharide, that has a specific binding mode upon infection to impart a host specificity to viruses, and by invading inside cells through endocytosis, and then changing its conformation and inducing the fusion of membranes. As to inhibitors of hemagglutinin, researches were conducted only from fundamental standpoints by using compounds comprised of a polyacrylamide bound by sialic acid (Mammen, M., et al., J. Med. Chem., 38, pp.4179–4190, 1995).

It is known that cholera toxin produced by Vibrio parahaemolyticus causes severe diarrhea. The toxin is composed of subunit A and subunit B. The subunit B, as a pentamer, acts as a receptor for a ligand, and has a role in introducing the subunit A as a toxic body, per se, into cytoplasm.

DESCRIPTION OF THE INVENTION

The object of the present invention is to provide a compound which exerts antiviral activity against variety of viruses and is useful as an active ingredient of a medicament. The inventors of the present invention conducted various studies to achieve the foregoing object, and as a result, found that a compound composed of a polymer containing a saccharide-conjugated sphingosine exhibited strong antiviral effect against viruses including influenza virus, for example. The present invention was achieved on the basis of these findings.

The present invention thus provides a polymer compound and a salt thereof which comprises a biodegradable polymer containing a glycosphingolipid. According to preferred embodiments of the present invention, the aforementioned polymer compound or a salt thereof wherein the glycosphingolipid is a lysoglycosphingolipid, more preferably lysoganglioside, and most preferably lysoganglioside $GM_3$ is provided. According to further preferred embodiments, the aforementioned polymer compound or a salt thereof wherein the glycosphingolipid and the biodegradable polymer are bound by means of a spacer; and the aforementioned polymer compound or a salt thereof wherein the biodegradable polymer is a polyglutamic acid, more preferably a polyglutamic acid acetylated at N-terminal thereof are provided. Sodium salts may preferably be used as the salt of the compound.

According to the most preferred embodiment of the present invention, it is provided a polymer compound represented by the following formula (I) and a salt thereof:

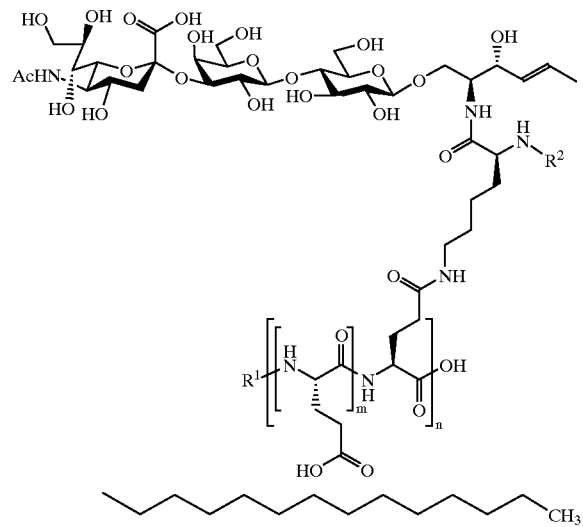

wherein $R^1$ represents hydrogen atom or acetyl group; $R^2$ represents hydrogen atom or a fluorescent functional group, and m and n independently represents an integer of from 10 to 40. According to a preferred embodiment of the aforementioned polymer compound and a salt thereof, there is provided the polymer compound and sodium salt thereof wherein $R^1$ is acetyl group, $R^2$ is a fluorescent functional group such as BODIPY group, m is an integer of from 15 to 25, n is an integer of from 20 to 40, and the amount of conjugated lysoganglioside $GM_3$ is from 1 to 10 molar percent. Among them, the polymer compound and sodium salt thereof wherein m is 19, n is 27, and the amount of the conjugated lysoganglioside $GM_3$ is 5 molar percent are most preferred.

According to another aspect of the present invention, there is provided a medicament comprising the aforementioned polymer compounds. According to preferred embodiment of the aforementioned invention, the medicament used as an antiviral agent and/or antidote is provided. According to further aspects of the present invention, there are provided a method for the treatment of an infectious disease caused by a virus or a microorganism, which comprises the step of administering a therapeutically effective amount of the aforementioned polymer compound to a patient; and lysoganglioside $GM_3$ derivatives represented by the following formula (II):

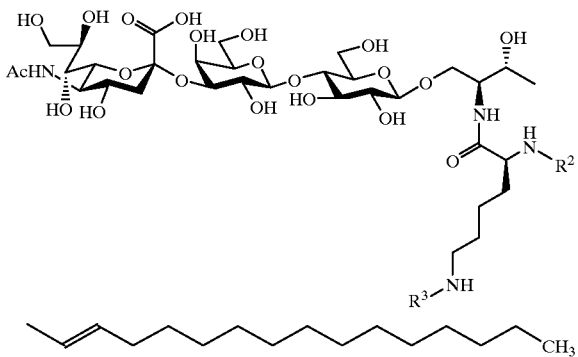

wherein R³ represents hydrogen atom or an amino protective group; and R⁴ represents hydrogen atom or a fluorescent functional group. The compound represented by the formula (II) is useful as a synthetic intermediate for the aforementioned polymer compound.

BEST MODE FOR CARRYING OUT THE INVENTION

The polymer compounds of the present invention are characterized in that they comprise a biodegradable polymer containing a residue of a glycosphingolipid. As glycosphingolipids from which the residue of a glycosphingolipid is derived, any glycolipids may be used so long as they contain a long chain amino alcohol having 16 to 20 carbon atoms (sphingoid). Glycolipids containing a sphingosine may preferably be used, and most preferably, a naturally occurring sphingosine [D(+)-erythro-1,3-dihydroxy-2-amino-4-trans-octadecene] may be used. As the residue of the glycolipid, which corresponds to a partial structure of the glycosphingolipid, for example, a residue of a glycolipid formed by the conjugation of a sialic acid residue and a saccharide residue, and a residue of a glycolipid formed by the conjugation of a sialic acid residue and a nonreducing terminal of an oligosaccharide residue composed of two or more saccharide residues may preferably be used.

As the residues of glycosphingolipids, for example, lysoglycosphingolipid residues may preferably be used. Among them, a lysoganglioside residue (the term "lysoganglioside" used herein means a ganglioside whose ceramide is deacylated, namely, a compound comprising a sialic acid-containing oligosaccharide chain bound to a sphingosine by means of a glycosidic linkage) is more preferred, and lysoganglioside $GM_3$ (Lyso $GM_3$) residue is most preferred.

Types of the biodegradable polymer are not particularly limited so long as they are readily degraded by enzymes existing in a living body, preferably in a human living body, and are substantially free from antigenicity and low toxic to a living body. Numbers of such biodegradable polymers are known, and an appropriate polymer is readily obtainable and used by one of those skilled in the art. For example, synthetic polymers as well as polypeptides, polynucleotides, polysaccharides and other may be used. When a serum half-life of the biodegradable polymer is too short, desired antiviral effects may sometimes be insufficiently achieved. On the other hand, if a serum half-life is too long, accumulation in a body may sometimes be a problem. Therefore, it is desired that a suitable type of biodegradable polymer may be chosen depending on the type of the glycosphingolipid, a desired biological action and other factors.

For example, polypeptides such as polyglutamic acid may preferably be used as the biodegradable polymer. When polyglutamic acids are used as the biodegradable polymer, for example, those having the degree of polymerization of about 100 to 1,000, preferably about 300 to 700, and most preferably about 500 to 600 can be used. In the polymer compounds represented by the general formula (I) mentioned above, it is preferred that m is an integer of from 15 to 25, n is an integer of from 20 to 40, and the amount of conjugated lysoganglioside $GM_3$ is 1 to 10 molar percent.

In the polymer compounds of the present invention, the biodegradable polymer may be directly bound to the residue of the glycosphingolipid, or alternatively, they may be bound by means of a suitable spacer. In general, as to the linkage between the biodegradable polymer and the residue of the glycosphingolipid, a carboxyl group existing in the biodegradable polymer and an amino group existing in the sphingoid may preferably participate in the linkage of both units. When both units are directly bound to each other, it is preferred that an acid amide bond is formed between the carboxyl group and the amino group.

For example, when both units are bound to each other by means of a spacer, a carboxyl group and an amino group of a spacer, which consists of one amino acid residue, may bind to an amino group of the sphingoid and a carboxyl group of the biodegradable polymer, respectively, to form acid amide bonds. Alternatively, it is preferred that a C-terminal and a N-terminal of an oligopeptide spacer consisting of two or more amino acid residues may bind to an amino group of the sphingoid and a carboxyl group of the biodegradable polymer, respectively, to form acid amide bonds. However, It should be understood that the spacers and the linkages between the biodegradable polymer and the glycosphingolipid residue are not limited to those explained above, and they can be appropriately chosen by one of ordinary skilled in the art from various available spacers and bonding modes. For example, diamino compounds, acid anhydrides and other may be reacted to use as a spacer, or ester bond and other may be used as the linkage.

For example, the polymer compound of the present invention may have a fluorescent functional group so that intracellular transmigration can be visually traced after coupling with a virus. The fluorescent functional group may preferably be bound to, for example, a spacer moiety. Types of the fluorescent functional group are not particularly limited. For example, BODIPY group (4,4-difluoro-5,7-dimethyl-4-bora-3α,4α-diaza-s-indacene-3-propionic acid) may be used. When the fluorescent functional group is bound to a spacer, tri-functional amino, e.g., lysine, may preferably be used as a spacer which consists of one amino acid.

The polymer compound of the present invention may exist as the form of a salt such as sodium salt and potassium salt, and may also exist as a hydrate or a solvate. Hydroxyl groups, carboxyl groups, amino groups or other of the polymer compound of the present invention may be protected by using suitable protective groups. The protective groups are not particularly limited, and any types of protective groups available to those skilled in the art can be utilized. The polymer compound of the present invention may also exist as isomers in a pure form such as optically active compounds or diastereoisomers, or alternatively, exist as mixtures thereof (racemates and mixtures of diastereoisomers). Any of the substances mentioned above fall within the scope of the present invention.

Among preferred polymer compounds of the present invention, a particularly preferred compound (sodium salt)

is shown below. However, the polymer compound of the present invention is not limited to the aforementioned particular compound. In the formula, m is 19, n is 27, and the amount of conjugated lysoganglioside $GM_3$ is 5 molar percent.

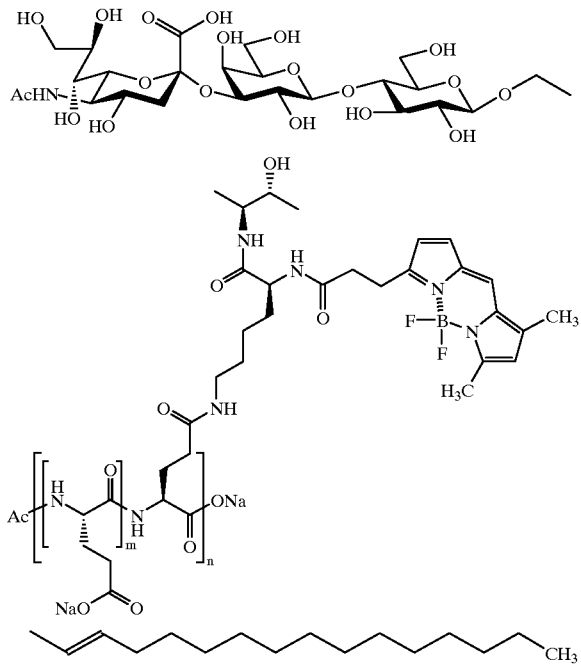

The polymer compound of the present invention, having a polar portion and a non-polar portion in the molecule, forms self micells in an aqueous solution, and behaves in the same manner as naturally occurring glycoproteins in a living body. Although it is not intended to be bound by any specific theory, the preferred polymer compound of the present invention shown as formula 5 is specifically recognized by a sialyloligosaccharide-recognizing receptor protein such as hemagglutinin of influenza virus and cholera toxin. After the conjugation with hemagglutinin, cholera toxin or other, the polymer compound changes its state from self-association to a linear chain structure, and strongly binds to side chains of hydrophobic amino acids of a protein or virus membranes by means of hydrophobic bond. Even if sialic acid is cleaved by sialidase deriving from influenza virus, the exposed galactose residues are caught by macrophages, and viruses, per se, are phagocytized by macrophages.

Accordingly, the polymer compound of the present invention is useful as an active ingredient of a medicament for preventive and/or therapeutic treatment of infectious diseases caused by viruses or microorganisms. In general, viruses have a feature of specifically recognizing a certain glycolipid or lipid, and therefore, a medicament which specifically acts on a specific virus or a microorganism can be produced by appropriately choosing a glycolipid portion of the glycosphingolipid residue of the polymer compound of the present invention. As an example, a polymer compound specifically acting on influenza virus is shown as formula 5. It is also possible to produce a medicament acting on plural viruses by choosing a glycolipid which is commonly recognized by several virus groups.

The medicament of the present invention may preferably be applicable to diseases such as, for example, viral hepatitis (type A, B, C, or E); influenza: virus pneumonitis; viral bronchitis; herpes infection, acute anterior poliomyelitis, AIDS, adult T cell leukemia, papilloma, measles, rubella, roseola infantum, erythema infectiosum, viral encephalitis, viral meningitis, cytomegalovirus infection, epidemic parotitis, chicken pox, hydrophobia, viral enteritis and the like. Among them, influenza is a particularly suitable target disease. However, diseases to which the medicament of the present invention is applicable are not limited to these viral diseases. The medicament of the present invention, in which the glycolipid portion of the polymer compound is appropriately chosen, may also be used for the treatment of infectious diseases caused by microorganisms such as bacteria.

The aforementioned polymer compound or a physiologically acceptable salt thereof may be used, per se, as the medicament of the present invention. However, it is generally preferred that a pharmaceutical composition for administration which comprises the above substance as an active ingredient is prepared by using additives for pharmaceutical preparations available to those skilled in the art. Although the route of administration of the medicament of the present invention is not particularly limited, it is preferred that the medicament is parenterally administered by using formulations such as injections, drip infusions, suppositories, inhalants, transmucosal preparations, transdermal preparations, nasal drops, ear drops and other. The medicament of the present invention may also be orally administered depending on a type of the biodegradable polymer. In that case, pharmaceutical preparations for oral administration such as tablets, capsules, powders, subtilized granules, granules, solutions, syrups and other can be used.

Examples of pharmacologically and pharmaceutically acceptable additives for pharmaceutical preparations include, for example, aqueous media such as distilled water for injection; solubilizers or solubilizing aids which can constitute injections dissolved before use; isotonic agents such as glucose; pH modifiers such as inorganic acids, organic acids, inorganic bases, and organic bases and the like. A dose of the medicament of the present invention should be suitably increased or decreased depending on various conditions such as a type of a disease, symptoms and the age of a patient, and a purpose of preventive or therapeutic treatment. The dose may be suitably chosen by those skilled in the art on the basis of these factors.

As an example of the method of preparation of the polymer compound, a method using lysoganglioside $GM_3$ as a synthetic intermediate, represented by the general formula (II) wherein $R^3$ is Fmoc group as an amino protective group and $R^4$ is BODIPY group, will be described below in Examples. Accordingly, any desired polymer compounds falling within the general formula (I) may be readily prepared by referring to these methods, or by appropriately modifying or changing starting materials, reagents, reaction conditions and other. However, the methods of preparation of the polymer compound of the present invention are not limited to those described in the following examples.

EXAMPLES

The present invention will be explained more specifically by referring to the following examples. However, the scope of the present invention is not limited to these examples.

Example 1

(a) N-terminus acetylated poly(L-glutamic acid succinimidyl ester)

10% $Na_2CO_3$ (about 150 $\mu l$) and acetic anhydride (60 $\mu l$) were added to an aqueous solution (1.0 ml) of poly-L- glutamic acid (43.4 mg). The reaction mixture was purified by Superose 12 pg column (Pharmacia Biotech) (eluent: water), and lyophilized to obtain an acetylated compound. To a suspension of the acetylated compound (32.1 mg), N-hydroxysuccinimide and EDC (N-ethyl-N'-3-dimethylamino-propylcarbodiimide-HCl, 6.1 mg) in DMF (25 ml), 1,4-dioxane (12.5 ml) and ethyl acetate (12.5 µl) were added at room temperature. The reaction mixture was stirred for 27 days. Insoluble substances were collected by filtration, and washed with ethyl acetate. The filtrate and the wash liquor were combined, and diluted with ethyl acetate. The organic layer was washed with water and saturated brine, dried over $Na_2SO_4$, and then evaporated under reduced pressure to obtain a succinimide compound (38.6 mg). $^1$H-NMR analysis verified that about 50% of the monomer units was esterified.

$^1$H-NMR($CDCl_3$): δ6.32 (m, NHα), 3.69(m, 1H, Cα-H), 2.8–2.9 (m, Cβ-H, Cγ-H), 2.82 (s, succinimide), $^{13}$C-NMR: δ169.7, 169.1, 167.0, 151.6, 37.3, 31.5, 25.5, 25.4.

(b) Nε-Fmoc-lysine

L-Lysine dihydrochloride (100 mg) was dissolved in boiled water (1 ml), and the solution was added with $CuCO_3Cu(OH)_2H_2O$ (70 mg). The mixture was filtered, and washed with water. The filtrate and the wash liquor were combined, and the resulting solution was made basic with 10% $Na_2CO_3$ aqueous solution (1 ml). A solution of 9-fluorenylmethyl succinimidyl carbonate (Fmoc-E) (184 mg, 1.2 equivalents) in 1,2-dimethoxyethane (4 ml) was added dropwise to the solution at 0° C. and mixed. After two hours, the reaction mixture was warmed up to ambient temperature, and then stirred overnight. Deposited green precipitates were collected by filtration and washed with water, EtOH and $Et_2O$, and then dried under reduced pressure.

A suspension of ethylenediaminetetraacetic acid (EDTA, 102 mg) in 0.33 M HCl (4 ml) was added to the precipitate. After three hours, white precipitates were collected by filtration and washed with water. The precipitates were dissolved in a hot solution composed of $EtOH/H_2O$ (7/3, v/v), and the insoluble substances were collected by filtration and washed with $EtOH/H_2O$ (7/3, v/v) solution. Crystals of Nε-Fmoc-lysine, precipitated from a combined solution of the filtrate and the wash liquor, were washed with EtOH and $Et_2O$ to become neutral, and then dried under reduced pressure to obtain the desired product (96.7 mg, 58.2%).

mp=188° C. (decomposition)

Rf=0.06 ($CHCl_3/CH_3OH/AcOH$=95/10/3, v/v/v)

$^1$H-NMR ($D_2O/CD_3OD$ (1/1, v/v), 25.5° C., ref 4.8 ppm): δ7.8 (d, 2H, Fmoc), 7.6 (d, Fmoc), 7.4 (t, Fmoc), 7.3 (t, Fmoc), 4.3–4.5, 4.1–4.3 (Fmoc), 3.5–3.7 (1H, Cα-H), 2.9–3.1 (m, 2H, Cε-H), 1.7–1.9 (dd, 2H, J=5.9, 10.6, Cβ-H), 1.2–1.4 (m, 2H, Cγ-H), 1.3–1.5 (m, 2H, Cd-H)

Anal. Calcd. For $C_{21}H_{24}O_4N_2$: C, 68.46; H, 6.57; N, 7.61. Found: C, 67.86; H, 6.56; N, 7.54.

(c) Nα-BODIPY—Nε-Fmoc-lysine

A solution of 4,4-difluoro-5,7-dimethyl-4-bora-3α,4α-diaza-s-indacene-3-propionic acid succinimidyl ester (BODIPY FL C3-SE, 3.0 mg, $7.7 \times 10^{-3}$ mM, 1 equivalent) in $CH_2Cl_2$ (1 ml) was added to a suspension of Nε-Fmoc-lysine (5.4 mg, $1.5 \times 10^{-2}$ mM, 2 equivalents) in MeOH (1 ml). To the suspension, 10% $Na_2CO_3$ aqueous solution (about 50 ml) was added at room temperature. The reaction mixture was stirred for two hours, and then diluted with ethyl acetate. The mixture was washed with 0.33 M HCl, water and brine and dried over $Na_2SO_4$, and then evaporated under reduced pressure. The residue was purified by PTLC (eluent: 20% $MeOH/CHCl_3$, v/v) to obtain Nα-BODIPY—Nε-Fmoc-lysine (4.3 mg, yield: 87%).

$[\alpha]^D$=−173° (c=0.40 in MeOH)

Rf=0.5 ($CHCl_3/CH_3OH/AcOH$=95/10/3, v/v/v)

$^1$H-NMR ($CDCl_3$): δ7.0 (NHα), 5.33(NHε), 4.3–4.4 (m, 1H, Cα-H), 3.03 (m, 2H, Cε-H), 1.76 (m, 2H, Cβ-H), 1.62 (m, 2H, Cγ-H), 1.33 (m, 2H, Cδ-H), 7.69 (d, 2H, J=7.5, Fmoc), 7.52 (d, 2H, J=7.3, Fmoc), 7.38 (t, 2H, J=6.9, Fmoc), 7.22 (t, 2H, J=7.3, Fmoc), 4.29 (d, J=6.3, Fmoc), 4.11 (broad dd, J=6.3, 13.2, Fmoc), 6.96 (s, 1H, BODIPY), 6.75 (d, 1H, J=4.0, BODIPY), 6.20 (d, 1H, J=3.3, BODIPY), 5.98 (s, 1H, BODIPY), 2.42 (s, 3H, BODIPY—$CH_3$), 2.12 (s, 3H, BODIPY—$CH_3$), 3.22, 2.63 (dd, dd, 2H, 2H, BODIPY—$CH_2$—)

FAB-MS calcd. for Pos[M+Na]$^+$: 665.,3, found: 665.3

(d) Nα-BODIPY-Nε-Fmoc-lysine succinimidyl ester 1,3-Diisopropylcarbodiimide (1.6 ml, 1.2 equivalents) was added to a solution of Nα-BODIPY-Nε-Fmoc-lysine (5.4 mg, $8.5 \times 10^{-3}$ mM) and N-hydroxysuccinimide (1.2 mg, 1.2 equivalents) in $CH_2Cl_2$ (1 ml) at 0° C. The reaction mixture was stirred for 2.5 hours and then diluted with ethyl acetate. The mixture was washed with 0.33 M HCl, water and brine and dried over $Na_2SO_4$, and then evaporated under reduced pressure to obtain Nα-BODIPY-Nε-Fmoc-lysine succinimidyl ester (8.1 mg).

Rf=0.33 (10% $CH_3OH/CHCl_3$, v/v)

$^1$H-NMR ($CDCl_3$): δ6.42 (broad d, NHα), 5.12 (broad t, NHε), 4.94 (m, 1H, Cα-H), 3.14 (m, 2H, Cε-H), 1.85 (m, 2H, Cβ-H), 1.49 (m, 2H, Cδ-H), 1.33 (m, 2H, Cγ-H), 7.75 (d, 2H, J=7.6, Fmoc), 7.58 (d, 2H, J=7.3, Fmoc), 7.38 (t, 2H, J=7.6, Fmoc), 7.29 (t, 2H, J=7.3, Fmoc), 4.38 (d, J=6.9, Fmoc), 4.18 (t, 1H, Fmoc), 7.07 (s, 1H, BODIPY), 6.85 (d, 1H, J=4.0, BODIPY), 6.27 (d, 1H, J=3.6, BODIPY), 6.09 (s, 1H, BODIPY), 2.54 (s, 3H, BODIPY—$CH_3$), 2.22 (s, 3H, BODIPY—$CH_3$), 3.29, 2.72 (broad t, m, 2H, 2H, BODIPY-$CH_2$—), 2.79 (s, 4H, succinimide).

(e) Nα-BODIPY-Nε-Fmoc-lysine-C-Lyso $GM_3$

Crude Nα-BODIPY-Nε-Fmoc-lysine succinimidyl ester compound (0.5 mg, about 5 equivalents), dissolved in a mixture of DMF and 100 mM triethylamine in methanol (7/3, v/v, 20 ml), was added to Lyso $GM_3$ (100 mg) dissolved in a mixture of DMF and 100 mM triethylamine in methanol (7/3, v/v, 20 ml). The reaction mixture was stirred at room temperature for two hours. This reaction mixture was concentrated under reduced pressure, and the residue was purified by PTLC (eluent:$CHCl_3$/MeOH/15 mM $CaCl_2$=60/35/8) to obtain Nα-BODIPY-Nε-Fmoc-lysine-C-Lyso $GM_3$ in a quantitative yield.

Rf=0.33 ($CHCl_3/CH_3OH$/15 mM $CaCl_2$=60/35/8, v/v/v)

600 MHz $^1$H-NMR ($CD_3OD$): δ7.68 (d, 2H, J=7.7, Fmoc), 7.53 (d, 2H, J=5.9, Fmoc), 7.28 (t, 2H, J=7.7, Fmoc), 7.19 (t, 2H, J=7.3, Fmoc), 7.30 (s, 1H, BODIPY), 6.90 (d, 1H, J=4.4, BODIPY), 6.22 (d, 1H, BODIPY), 6.10 (s, 1H, BODIPY), 3.13 (m, 2H, —$CH_2$—, BODIPY), 2.58 (m, 2H, —$CH_2$—, BODIPY), 2.41 (s, 3H, BODIPY—$CH_3$), 2.16 (s, 3H, BODIPY—$CH_3$), 4.2 (1H, Cα-H), 2.99 (m, 2H, Cε-H), 1.63 (m, 2H, Cβ-H), 1.5 (m, 2H, Cγ-H), 1.39 (m, 2H, Cδ-H), 4.20–4.24 (1H, Glc-H-1), 4.32 (d, 1H, J=7.7, Gal-H-1). 3.95 (dd, 1H, J=2.9, 9.9, Gal-H-3), 3.84 (broad s, 1H, Gal-H-4), 2.76 (dd, 1H, Neu5Ac-H-2eq.), 1.6 (1H, Neu5Ac-H-2ax.), 1.91 (3H, Neu5Ac-NHCOCH$_3$), 5.31–5.36 (m, 1H, sphingosine-olefinic R-4), 5.56–5.61 (m, 1H, sphingosine-olefinic R-5), 1.19 (16H, sphingosine methylene), 0.79 (sphingosine terminal methyl)

ESI-MS calcd. for Pos[M+2Na−H]$^+$: 1584, found: 1584; calcd. for Neg[M−H]$^-$: 1538, found: 1538.

(e) Nα-BODIPY-lysine-C-Lyso $GM_3$

Piperidine (50 ml) was added to a solution of Nα-BODIPY—Nε-Fmoc-lysine-C-Lyso $GM_3$ (about 0.2 mg) in DMF (50 ml). This reaction mixture was stirred at room temperature for two minutes, and concentrated under $N_2$ flow. The residue was purified by PTLC (eluent: $CHCl_3$/MeOH/15 mM $CaCl_2$=60/35/8) to obtain Nα-BODIPY-lysine-C-Lyso $GM_3$ in a 34.6% yield (absorption about 505 nm was determined by spectrophotometry).

Rf=0.27 ($CHCl_3/CH_3OH$/15 mM $CaCl_2$=60/35/8, v/v/v)

600 MHz $^1$H-NMR ($CD_3OD$): δ7.34 (s, 1H, BODIPY), 6.93 (d, 1H, BODIPY), 6.26 (d, 1H, BODIPY), 6.13 (s, 1H, BODIPY), 3.13 (m, 2H, —$CH_2$—, BODIPY), 2.62 (t, 2H, —$CH_2$—, BODIPY), 2.42 (s, 3H, BODIPY—$CH_3$), 2.19 (s, 3H, BODIPY—$CH_3$), 4.2–4.3 (1H, Cα-H), 3.03 (m, 2H, Cε-H), 1.5–1.65 (m, 4H, Cβ-H, Cγ-H), 1.69 (m, 2H, Cδ-H), 4.21 (d, 1H, J=8.1, Glc-H-1), 4.32 (d, 1H, J=8.1, Gal-H-1), 3.93–3.95 (1H, Gal-H-3), 3.80 (broad s, 1H, Gal-H-4), 2.81 (dd, 1H, Neu5Ac-H2eq.), 1.54 (1H, Neu5Ac-H2ax.), 1.91 (3H, Neu5Ac-$NHCOCH_3$), 5.32–5.38 (m, 1H, sphingosine-olefinic R-4), 5.56–5.59 (m, 1H, sphingosine-olefinic R-5), 1.19 (16H, sphingosine methylene), 0.80 (sphingosine terminal methyl), ESI-MS calcd. for Pos$[M+2Na-H]^+$: 1362, found: 1362; calcd for Neg$[M+Na]^+$: 1340, found: 1340; calcd for Neg $[M-H]^-$: 1316, found: 1316

(f) Preparation of the Polymer Compound of the Present Invention

A solution of Nα-BODIPY-lysine-C-Lyso $GM_3$ (about 0.04 mg) in $CH_2Cl_2$/MeOH (7/3, v/v, 400 μl) was added to a solution of N-terminus acetylated poly(L-glutamic acid succinimidyl ester) (0.8 mg) in $CH_2Cl_2$/MeOH (7/3, V/v, 100 μl). The reaction mixture was stirred at ambient temperature overnight. The mixture was concentrated under reduced pressure and purified by Superose 12 pg column (Pharmacia Biotech, eluent:water), and then evaporated under reduced pressure to obtain a polymer compound of the present invention quantitatively. The $GM_3$-content of the compound (%) was determined by using an agent for coupling reaction on the basis of 5% of the glutamic acid units, and then further verified by NMR analysis.

270 MHz $^1$H-NMR ($D_2O$): δ3.6–3.8 (m), 3.3–3.4 (m), 2.4–2.6 (m), 1.98, 1.96 (s, $CH_3$), 0.86 (sphingosine terminal methyl).

GPC analysis of the above polymer compound was performed by using Waters 600E System Controller, 486 revolving type spectrophotometer, and Yokogawa LC100 System Column Oven. Waters Ultrahydrogel Liner (7.8 i.d.×300 mm) was used as a column, and elution was performed with 0.1M $NaNO_3$ at a flow rate of 1 ml/minute. Detection was carried out at 40° C. by u.v. at 500 nm or refraction index. Millenium 2010 and GPC software were used for data analysis. Polyethylene oxide was used as a standard.

HPLC-GPC profile: Mw=175,017, Mw/Mn=2.10.

Example 2

Action on Cholera Toxin B (CTB)

Ganglioside $GM_{1a}$ (660 pmol, 1 μl solution) was spotted on a PVDF membrane and blocked by a treatment using 1% BSA solution at room temperature for two hours, and then washed with phosphate buffered physiological saline (5 minutes, 5 times). The membrane was incubated at 37° C. for 2 hours with A) horseradish peroxidase (POD) conjugated cholera toxin B (CTB: 660 pmol as monomer) (CTB-POD), or B) CTB-POD which had been pre-incubated at 37° C. for 1 hour in the presence of the compound of the present invention obtained in Example 1 (660 pmol as $GM_3$), and washed with phosphate buffered physiological saline (5 minutes, 5 times). The CTB bound to the membrane was visualized by adding POD Immunostain Set (Wako Pure Chemicals Industries., Co., Ltd.) containing Nitrotetrazolium Blue (NTB), phenol, hydrogen peroxide, and NADH, and then treated at room temperature for ten minutes. As a result, the compound of the present invention obtained in Example 1 was found to achieve almost complete inhibition against the binding of cholera toxin B and ganglioside $GM_{1a}$.

Example 3

Action on Cholera Toxin B

Inhibitory activity of the compound of the present invention (Example 1) against cholera toxin B was assayed by the ELISA method as follows. An aqueous solution containing 50 pmol of $GM_{1a}$ was added to a nitrocellulose (NC) membrane placed in each well of a 12-well microwell blotter plate. The solution was allowed to penetrate into the NC membranes at room temperature for ten minutes, and then the solvent was removed by filtration. Then, the binding sites remained on the membranes were blocked by a treatment with 25 ml of water containing 1% BSA for three hours at room temperature. After the treatment, the BSA solution was removed and the NC membranes were washed four times with 250 ml of water.

Serial double-fold dilutions of the compound of the present invention (200 pmol) diluted with water were pre-incubated with an aqueous solution containing 50 pmol of the CTB-POD conjugate at room temperature for three hours. The mixture was added to each of the wells, and then incubated with the membranes at room temperature for three hours. After washed six times with water, the membranes were allowed to react with 25 ml of POD Immunostain Set (Wako Pure Chemicals Industries, Japan) at room temperature for ten minutes to detect CTB-POD bound to the $GM_{1a}$ immobilized on the membranes. The reaction was stopped by adding water, and CTB-HRP binding activity in the form of color development was determined by using ATTO Densitograph Software Library Lane Analyzer (ATTO Corporation, Japan). The analysis was performed by using serial double-fold dilutions of $GM_{1a}$ (200 pmol) and $GM_3$ (25.6 nmol) as controls. The results are shown in Table 1 (in the table, the parenthesized $IC_{50}$ value appended with * is a value per one sialic acid residue).

TABLE 1

| Test substance | $IC_{50}$ per molecule (mol) |
|---|---|
| Compound of the present invention (1.42) | $5.5 \times 10^{-12}$<br>$(4.2 \times 10^{-11})^*$ |

TABLE 1-continued

| Test substance | IC$_{50}$ per molecule (mol) |
| --- | --- |
| GM$_3$ | 1.5 × 10$^{-9}$ |
| GM$_{1a}$ | 1.6 × 10$^{-11}$ |

Example 4

Action of Binding to Influenza Virus

Binding to influenza virus [human influenza virus A/PR/8/34(H1N1)] which recognizes sialyl 2–3 galactose was examined by using ganglioside GM$_3$ separated and purified from human placenta and the compound of the present invention prepared in Example 1. An ethanol solution was prepared for each of GM$_3$ and the compound of the present invention prepared in Example 1 (20 nmol/ml as sialic acid), and serially diluted using ethanol by double-fold dilution from the stock solution to 1024-fold dilution. Each dilution (50 µl) was added to each well of a microtiter plate, and the plate was left stand at 37° C. to evaporate the ethanol. Then, 200 µl of phosphate buffer (pH 7.0) containing 5% bovine serum albumin was added to each well, and left stand for more than 12 hours.

The plate was washed with phosphate buffer, and 50 µl of a suspension of human influenza virus A/PR/8/34(H1N1), which was prepared at 32 HAU with phosphate buffer containing 0.2% bovine serum albumin, was added to each well, and the mixture was allowed to react at 4° C. for 12 hours. After each well was washed with phosphate buffer, 50 µl of rabbit anti-A/PR/8/34(H1N1) antibodies, diluted 500 times with phosphate buffer containing 0.2% bovine serum albumin, was added and then the mixture was allowed to react at 4° C. for three hours. After each well was washed with phosphate buffer, 50 µl of a solution of horseradish peroxidase-conjugated protein A, diluted 1000 times with phosphate buffer containing 0.2% bovine serum albumin, was added and then the mixture was allowed to react at 4° C. for two hours.

After each well was washed with phosphate buffer, 100 µl of a substrate solution containing O-phenylenediamine (0.4 mg/ml) and 0.01% hydrogen peroxide in 0.1M citrate-phosphate buffer (pH 5.0) was added, and the mixture was allowed to react at 25° C. for 15 minutes. Then, the reaction was stopped by adding 100 µl of 0.4 N sulfuric acid solution to each well, and color development as a result of binding to influenza virus was observed at measuring wavelength of 492 nm and control wavelength of 630 nm by using a microplate reader (Corona). The results revealed that the compound of the present invention has at least 16 times stronger binding activity compared to ganglioside GM$_3$ as a reference compound.

Example 5

Inhibitory Activity on Influenza Virus

Inhibitory activity of the compound of the present invention (Example 1) against influenza virus A/PR/8/34(H1N1) was assayed by the enzyme linked immunosorbent assay method (ELISA) as follows. An ethanol solution containing 1 nmol of GM$_3$ was added to each well of a 96-well microwell plate, and the solvent was evaporated at 37° C. Then, each well was treated with 200 µl of PBS containing 2% BSA at 4° C. for 12 hours to block binding sites remained on the wells. Serial double-fold dilutions of the compound of the present invention (200 pmol) in 0.2% BSA-PBS were pre-incubated with 50 µl of influenza virus suspension (32 HAU) at 4° C. of for two hours, and then added to the wells after the plate was washed five times with PBS.

The plate was incubated at 4° C. for 12 hours. After the plate was washed with PBS five times, 50 µl of anti-influenza virus antibodies diluted 1000 times with 0.2% BSA-PBS was added to each well and the plated was incubated at 4° C. for two hours, and then the mixture was allowed to react with HRP-conjugated protein A diluted with the solution A (1000 times) at 4° C. for 2 hours. The virions bound to GM$_3$ immobilized on the wells were detected by using o-phenylenediamine (OPD) solution containing 4 mg of OPD and 0.01% H$_2$O$_2$ in 100 mM phosphate-citrate buffer (pH 5.0). The reaction was stopped with 4N H$_2$SO$_4$, and binding activity to virus was determined by observing color development at 492 nm using a reference wavelength of 630 nm. Experiments were carried out by using serial double-fold dilutions of sialyl lactose (2 µmol), PGA (800 pmol) and Lyso GM$_3$ (20 nmol) as controls. The results are shown in Table 2 (in the table, the parenthesized IC$_{50}$ value appended with * is a value per one sialic acid residue, and the result appended with ** indicates that no inhibition by PGA used as control was observed within the concentration range applied in the assay up to the maximum concentration of 1×10$^{-9}$ mol).

TABLE 2

| Test substance | IC$_{50}$ per molecule (mol) |
| --- | --- |
| Compound of the present invention | 1.9 × 10$^{-12}$ (7.5 × 10$^{-12}$)* |
| GM$_3$ | 1.0 × 10$^{-9}$ |
| Lyso GM$_3$ | 3.0 × 10$^{-9}$ |
| Sialyl lactose (GM$_3$ oligosaccharide) | 1.5 × 10$^{-7}$ |
| PGA | No inhibition** |

In addition, when the compound of the present invention (Example 1) was added to a virus solution, an increase of fluorescence emission of BODIPY ($\lambda_{em}$: 510 nm, $\lambda_{ex}$: 480 nm) was immediately observed. The result suggests that the compound of the present invention in a folded form was changed to a defolded form. Then, an additional incubation at 10° C. gave a decrease of luminescence intensity. The result can be interpreted that an energy transfer was occurred to the aromatic amino acid residue of hemagglutinin (HA). Accordingly, these results indicated that (A) the compound of the present invention having a specific ligand (sialyl lactose for the compound of Example 1) (as a folded structure) approached to hemagglutinin (HA), (B) and then interaction occurred between the ligand and the receptor so as to defold the compound of the present invention, and (C) hydrophobic interaction occurred between the defolded compound of the present invention and hemagglutinin to form a more stable complex.

INDUSTRIAL APPLICABILITY

The polymer compounds of the present invention are useful as an active ingredient of a medicament used for preventive and/or therapeutic treatment of viral infections.

What is claimed is:

1. A polymer compound or a salt thereof which comprises polyglutamic acid containing glycosphingolipid, said polymer represented by the following formula:

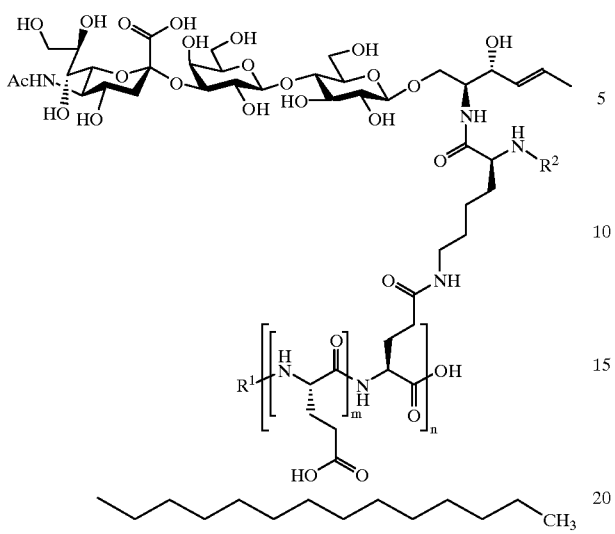

wherein R¹ represented hydrogen atom or acetyl group; R² represents hydrogen atom or a fluorescent functional group; and m and n independently represent an integer of 10 to 40, or a salt thereof.

2. The polymer compound or a salt thereof according to claim 1, wherein R¹ is acetyl group, R² is 4,4-difluoro-5,7-dimethyl-4-bora-3α,4α-diaza-s-indacene-3-propionic acid, m is 19, n is 27, and the amount of conjugated lysoganglioside GM₃ is 5 molar percent.

3. The polymer compound or a salt thereof according to claim 1, wherein the glycosphingolipid is lysoganglioside GM₃.

4. A polymer compound or a salt thereof according to claim 1, wherein said polyglutamic acid containing glycosphingolipid is acetylated at the N-terminal.

5. The polymer compound or a salt thereof according to claim 4, wherein the glycosphingolipid is lysoganglioside GM₃.

6. A composition which comprises as an active ingredient the polymer compound or a physiologically acceptable salt thereof according to claim 1.

7. A method of inhibiting influenza or cholera infectious agent replication by administering the composition of claim 6 in an amount effective to inhibit replication of the influenza or cholera infectious agent, and thereby inhibiting replication.

8. The method according to claim 7, wherein the composition is administered as an antiviral agent.

9. The method according to claim 7, wherein the composition is administered as an antidote.

10. The method according to claim 7, wherein the infectious agent is cholera.

11. The method according to claim 7, wherein the infectious agent is influenza virus.

12. A lysoganglioside GM₃ derivative represented by the following formula (II):

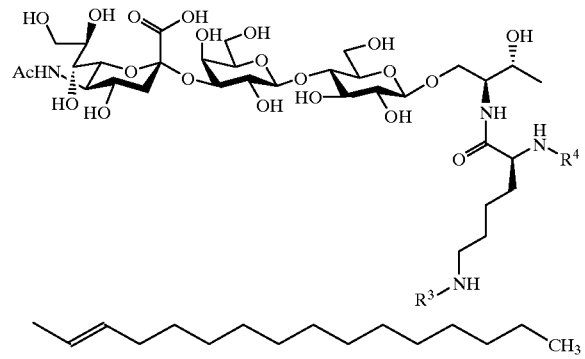

wherein R³ represents hydrogen atom or a amino protective group, and R⁴ represents hydrogen atom or a fluorescent functional group.

* * * * *